(12) United States Patent
Hollstein

(10) Patent No.: US 10,209,179 B2
(45) Date of Patent: Feb. 19, 2019

(54) DETERMINING A WEED PERCENTAGE AND AGRICULTURAL CONTROL DEVICE

(71) Applicant: Continental Automotive GmbH, Hannover (DE)

(72) Inventor: Armin Hollstein, Pfatter (DE)

(73) Assignee: CONTINENTAL AUTOMOTIVE GMBH, Hanover (DE)

(*) Notice: Subject to any disclaimer, the term of this patent is extended or adjusted under 35 U.S.C. 154(b) by 0 days.

(21) Appl. No.: 15/533,329

(22) PCT Filed: Dec. 8, 2015

(86) PCT No.: PCT/EP2015/078918
§ 371 (c)(1),
(2) Date: Jun. 5, 2017

(87) PCT Pub. No.: WO2016/096526
PCT Pub. Date: Jun. 23, 2016

(65) Prior Publication Data
US 2018/0024050 A1    Jan. 25, 2018

(30) Foreign Application Priority Data
Dec. 17, 2014   (DE) .................. 10 2014 226 189

(51) Int. Cl.
*G01N 21/27*    (2006.01)
*A01M 7/00*    (2006.01)
(Continued)

(52) U.S. Cl.
CPC ........... *G01N 21/27* (2013.01); *A01C 21/007* (2013.01); *A01G 22/00* (2018.02); *A01M 7/0089* (2013.01);
(Continued)

(58) Field of Classification Search
CPC ........ A01G 22/00; A01G 1/001; G01N 21/27; G01N 33/0098; A01M 21/043;
(Continued)

(56) References Cited

U.S. PATENT DOCUMENTS

| 5,144,767 A | 9/1992 | Mccloy et al. ............... 47/1.7 |
| 5,606,821 A | 3/1997 | Sadjadi et al. ............... 47/1.7 |

(Continued)

FOREIGN PATENT DOCUMENTS

| DE | 68912126 D1 | * | 2/1994 | ............. B05B 12/12 |
| DE | 68912126 T2 |  | 6/1994 | ............. A01M 7/00 |

(Continued)

OTHER PUBLICATIONS

German Office Action, Application No. 102014226189.9, 7 pages, dated Jun. 24, 2015.
(Continued)

*Primary Examiner* — Gregory F Cunningham
(74) *Attorney, Agent, or Firm* — Slayden Grubert Beard PLLC

(57) ABSTRACT

The present disclosure relates to agriculture. The teachings thereof may be embodied in methods to determine a percentage of weeds and/or control device. For example, a method for determining a weed percentage in an observation section of a field may include: acquiring actual spectral information using an optical observation section sensor aimed at the observation section; acquiring reference spectral information using an optical reference sensor aimed at a reference section of the same ground area; determining a difference between the actual spectral information and the reference spectral information; and mapping the difference to the weed percentage using predefined mapping.

10 Claims, 1 Drawing Sheet

(51) Int. Cl.
  *A01M 9/00* (2006.01)
  *A01C 21/00* (2006.01)
  *G06T 7/90* (2017.01)
  *A01G 22/00* (2018.01)
  *A01M 21/04* (2006.01)
  *G01J 3/457* (2006.01)
  *G01N 33/00* (2006.01)

(52) U.S. Cl.
  CPC ........ *A01M 9/0092* (2013.01); *A01M 21/043* (2013.01); *G01J 3/457* (2013.01); *G01N 33/0098* (2013.01); *G06T 7/90* (2017.01); *G06T 2207/10024* (2013.01); *G06T 2207/30188* (2013.01)

(58) Field of Classification Search
  CPC ........... G01J 3/457; G06T 2207/30188; G06T 2207/10024; G06T 7/90; A01C 21/007
  USPC ........................................................ 382/103
  See application file for complete search history.

(56) References Cited

U.S. PATENT DOCUMENTS

2002/0024665 A1  2/2002  Masten ............... 356/328
2008/0291455 A1  11/2008  Holland ............... 356/445

FOREIGN PATENT DOCUMENTS

| DE | 102011120858 A1 | 6/2013 | ............ A01G 7/00 |
| WO | 2016/096526 A1 | 6/1916 | ............ A01C 21/00 |
| WO | 98/21943 A1 | 5/1998 | ............ A01B 79/00 |
| WO | 99/19824 A1 | 4/1999 | ............ G01J 3/28 |

OTHER PUBLICATIONS

International Search Report and Written Opinion, Application No. PCT/EP2015/078918, 16 pages, dated Mar. 18, 2016.

* cited by examiner

DETERMINING A WEED PERCENTAGE AND AGRICULTURAL CONTROL DEVICE

CROSS-REFERENCE TO RELATED APPLICATIONS

This application is a U.S. National Stage Application of International Application No. PCT/EP2015/078918 filed Dec. 8, 2015, which designates the United States of America, and claims priority to DE Application No. 10 2014 226 189.9 filed Dec. 17, 2014, the contents of which are hereby incorporated by reference in their entirety.

TECHNICAL FIELD

The present disclosure relates to agriculture. The teachings thereof may be embodied in methods to determine a percentage of weeds and/or control device for herbicides.

BACKGROUND

Herbicides sprayed over a field area combat unwanted plants ("weeds") mixed within wanted crops. To optimize use, the field area may be treated with a varying dose of the herbicide based on the weed percentage (for instance the affected area percentage based on the total area considered).

The document DE 689 12 126 T2 describes the practice of detecting the reflectivity of a target area for particular bands of the electromagnetic spectrum, the relevant recorded values being compared with values in a particular look-up table. On the one hand, the detection of a reflectivity is susceptible to errors in the case of strong changing outside light irradiation. On the other hand, the storage of look-up tables and the comparison with the latter require a large amount of computational effort which increases with the quality of the adaptation to light conditions. In addition, the values in said look-up tables must also take into account the respective growth state of the plants, which additionally drives up their range.

SUMMARY

The teachings of the present disclosure may be used to optimize the sensor-based application of herbicides in a simple manner. For example, some embodiments may include a method for determining a weed percentage in an observation section (10) of a field (20). Methods may include acquiring an item of actual spectral information using at least one optical observation section sensor (12a, b) which is aimed at the observation section (10); acquiring an item of reference spectral information using an optical reference sensor (32) which is aimed at a reference section (30) of the same ground area (22); determining a difference between the actual spectral information and the reference spectral information; and mapping the difference to the weed percentage using predefined mapping.

In some embodiments, the reference section (30) and the observation section (10) comprise regions of the same agricultural field (20), arranged close together or at least partially overlapping.

In some embodiments, the reference sensor (32') is fastened on an area of the field (20) over which the observation section (10) or the at least one optical observation section sensor (12a, b) is guided.

In some embodiments, the actual spectral information and the reference spectral information characterize at least one spectrum interval, in particular a spectrum interval which comprises a visible region and/or an infrared and/or UV region, the actual spectral information and the reference spectral information each being present as a value or as a sequence of values relating to different wavelengths.

In some embodiments, the actual spectral information and/or the reference spectral information being acquired using color sensors (12a, b; 32) or electronic cameras, a color detection unit which determines color values over the entire image or over an image section from the cameras being connected downstream of the cameras. In some embodiments, shading of the observation section and of the reference section also being determined, and, in the case of different shading, the actual or reference spectral information or the difference between the actual and reference spectral information being adapted by means of arithmetic combination with a predefined lighting correlation variable.

In some embodiments, the methods include aligning the reference sensor (32; 32') with a reference area which does not have a weed percentage or has a tolerable weed percentage.

As another example, an agricultural control device (100) may include: at least one optical observation section sensor (112a, b), a reference sensor receiving interface (133) and an optional optical reference sensor (132), the observation section sensor (112a, b) and the reference sensor receiving interface (133) being fastened to the same vehicle; a comparator (140) which is connected downstream of the sensors (112a, b; 132, 132') and is set up to compare actual spectral information from the at least one observation section sensor (112a, b) with reference spectral information from the optical reference sensor (132, 132'); and a mapping unit (150) which is connected downstream of the comparator (140) and is set up to map the comparison result from the comparator (160) to a weed percentage and to output it at an output (160) of the agricultural control device (100).

In some embodiments, the reference sensor receiving interface (133) being set up to be connected to the optical reference sensor in the form of a static reference sensor (132') via a wireless data connection.

In some embodiments, there is a color detection unit (170) connected downstream of the at least one optical observation section sensor (112a, b) and/or the reference sensor receiving interface (133), the reference sensor (132) or the at least one optical observation section sensor (112a, b) being designed to record an electronic image and the receiving interface (133) being designed to receive an electronic image.

DETAILED DESCRIPTION

Figure 1:
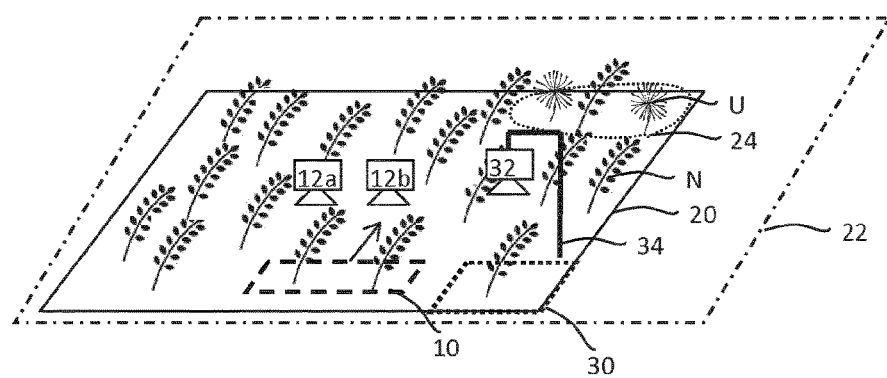
FIG. 1 is used to explain an embodiment of the method described above in more detail.

The teachings herein may be used to determine the spectrum of an observation section (which is possibly treated with plant protection agents) of a field to be compared with a spectrum of a section of the same field. Therefore, the reference sensor looks directly at a field section containing only crops (or crops with an admissible weed percentage). In particular, the reference sensor looks at the same field as a so-called observation section sensor which is aimed at an observation section whose weed percentage is determined. The reference sensor therefore acquires the spectral information under the same conditions (in particular light conditions and growth stage) as that sensor which is aimed at that section of the field (that is to say at that observation section) whose weed percentage needs to be determined. Therefore, the weed percentage results directly from a comparison of the spectral information from the two sensors, in particular since other influences (as in the case of prefabricated look-up tables) are ruled out.

In some embodiments, the reference sensor is static. The reference sensor can be set up, for instance, at the edge of the field, for instance by means of a holder such as a stand. The result is an item of actual spectral information relating to an observation section and an item of reference spectral information relating to a reference section, the actual spectral information and the reference spectral information being determined under the same acquisition conditions (for instance lighting, degree of development of the plants, light reflection of the ground etc.). The same acquisition conditions (or at least acquisition conditions which have a known relationship with respect to one another) result in the same manner for the observation section and the reference section. Therefore, the spectral acquisition is more precise and is immune to external influence (for example the change in the imaging or lighting).

A method for determining a weed percentage in an observation section of a field may include an item of actual spectral information and an item of reference spectral information being acquired. The actual spectral information is acquired using at least one sensor which is aimed at the observation section, whereas the reference spectral information is acquired using a preferably identical sensor which is aimed at a reference section. The sensors are optical sensors and are able to sense the intensity of at least two light wavelengths for the field of view of the sensor. The field of view of the respective sensor can correspond to the relevant section or can comprise the latter (in addition to other image sections).

The reference section and the observation section are sections of the same field or of the same field area, e.g., the crops in both sections were sown at the same time and are therefore in the same growth phase. The local vicinity results in the same acquisition conditions, with the result that different light conditions occur when determining the difference between the spectral information. The actual spectral information and the reference spectral information may be recorded at an interval of time with respect to one another which is not greater than a predetermined duration. This duration is such that it can be assumed that no changes in the light conditions, which can result in different measurement results (e.g., different weed percentages), arise within the interval of time. The duration may be 1 or 0.5 seconds, for example.

Both the actual spectral information and the reference spectral information can be averaged (for instance over a time window) or can be subjected to low-pass filtering before determining the difference. In some embodiments, outliers of the relevant spectral information which are detected on the basis of change rates above a predefined threshold value can be excluded from the acquisition or the further processing. Furthermore, outliers in the determined differences can be excluded from the further processing, outliers being detected from the fact that the magnitude of a difference value exceeds a predetermined limit.

For instance, if the reference sensor is shaded (by individual clouds or shadowing) and the observation section sensor is not shaded (or vice versa), the result may be outliers which are suppressed when determining the difference or during mapping. The time window can depend on the speed at which the observation section is guided over the field. The greater the speed, the shorter the time window may be. In some embodiments, the measuring rate at which the observation section sensor acquires the actual spectral information is dependent on this speed. The greater the speed, the greater the measuring rate is selected to be.

In some embodiments, the measuring rate or the time window may depend on the size of the field of view of the observation section sensor. Furthermore, the time window may depend on the area which is covered by a jet of spray which is controlled according to the detected weed percentage. The greater the field of view or the above-mentioned area, the shorter the time window is selected to be or the higher the measuring rate is.

A sensor for sensing the observation section is referred to as an observation section sensor on account of this function, and the sensor for sensing the reference section is referred to as a reference section sensor on account of this function. Different sensors are used to sense the reference section and the observation section.

A difference between the actual spectral information and the reference spectral information may be determined. The difference may be a mathematical difference value or a difference function or difference sequence which represents the difference in the intensity for particular wavelengths or for particular wavelength intervals (for one wavelength or summed over the relevant wavelength interval). The difference may also be given by a correlation between the spectral information, in which case a high correlation corresponds to a slight difference and vice versa.

The difference is mapped to the weed percentage by means of predefined mapping. The mapping can be implemented as an assignment of difference values to weed percentages in the sense of a table having two columns or as a function, as a parameter set of a function or as an algorithm. A first difference which is greater than a second difference is linked to a weed percentage which is greater than the weed percentage linked to the second difference. In other words, the mapping corresponds to a rising function, e.g., a monotonously rising function or a strictly monotonously rising function. The function may be continuous or may have discrete values (with respect to the weed percentage and the difference). Interpolation methods may be used during mapping if only differences having discrete values are assigned to weed percentages having discrete values, but the determined difference is between two differences which are present (and are linked to weed percentages). In some embodiments, the mapping is implemented by a microprocessor and a table containing differences and associated weed percentages, a first memory (section) for a program set up to carry out the method and a second memory (section) being connected to the microprocessor, and the second memory storing the differences and the associated weed percentages in a retrievable manner.

A plurality of observation sections may be sensed using a plurality of observation section sensors. Each observation section or each item of actual spectral information from each relevant sensor is processed by a separate comparator subunit and a separate mapping subunit. Furthermore, a controllable nozzle may be provided for each observation section (and therefore also for each sensor or for each associated comparator and mapping subunit). A (physically independent) module may be provided for each nozzle, e.g., on the nozzle, each module having a comparator subunit and a downstream mapping subunit. Each module has an output (or a subunit thereof) which is used to control an associated nozzle. A comparator subunit, a downstream mapping subunit, the relevant output, and an input for the reference spectral information are provided in each module. The observation section sensor connected to the comparator subunit may be integrated in this module. In addition, the relevant controllable nozzle may be integrated in the module. If a spray boom, for instance, is used as the agricultural apparatus, these modules or at least the observation sensors are lined up along this spray boom, e.g., in one or more rows. The modules are situated on the nozzle controlled by the respective module, or the relevant nozzle is integrated in the relevant module.

Herein, the hardware which is used to carry out the comparison and mapping operations described here is referred to as the mapping unit and comparator unit. These units may be physically distributed and may be implemented as physically distributed subunits as described above. Therefore, the term "unit" should not be considered physically but rather functionally. In some embodiments, there is a bus or another data network used to distribute the reference spectral information from a relevant input interface (or directly from the reference sensor) to the individual modules or subunits or their inputs.

Some methods include evaluation of the spectral information, which may relate to a plurality of spectral sections. In some embodiments, there is a plurality of threshold values (in particular as a vector) each relating to a different section of the spectrum. The difference results from a combination of the comparison results (which result with the individual threshold values), for instance a sum of the comparison results or a sum of the magnitudes of the comparison results. Logical combinations, in which case the number of times the threshold values are exceeded is evaluated, for instance, or is decisive for the weed percentage, or the instances in which the threshold values are exceeded may be combined by means of a logical combination. The comparison results may be combined with one another in weighted form since some spectral sections are more significant for the weed percentage than others.

An exemplary implementation of the mapping may include predefining a threshold value (or a threshold value vector) with which the difference (or a difference vector) is compared. (Vectors are used if a scalar quantity is respectively determined as the difference for a plurality of spectral sections). If the difference (or its magnitude in the case of a vectorial comparison) is not above the threshold value or is not above the threshold value with more than a predefined margin, a weed percentage is output which is less than a weed percentage which is output if the threshold value is exceeded.

In a simple case, a weed percentage of zero is output if the threshold value is not reached, and a weed percentage of greater than zero (for instance a constant, in particular a one) is output if the threshold value is reached or exceeded. If a zero is therefore output as the weed percentage, this corresponds to an observation section without weeds or with a (predefined) acceptable portion of weeds not requiring any treatment. If a one or the constant is output, this corresponds to an observation with weeds to an extent requiring treatment. The one (or the constant) can therefore be considered an activation signal (for the treatment of plants, e.g., for the delivery of plant protection agents), whereas, in the case of a zero, the treatment of plants or generally the delivery of (fertilizer or) plant protection agent is not active. Since the weed percentage is closely linked to the control of a field sprayer (a high weed percentage is synonymous with the need to activate the field sprayer), the term "weed percentage", in addition to the actual proportion or area of weeds between crops, may correspond to the variables "flow volume", "mass", "flow speed" or, in particular, "area concentration" of plant protection agent.

If a plurality of observation section sensors are used, e.g., one sensor for each nozzle or spray valve, the ratio of two differences between reference and actual spectral information can be used as the input variable for the mapping.

As noted above, the reference section and the observation section are regions of the same agricultural field arranged close together. In some embodiments, the sections may at least partially overlap. In some embodiments, the actual and reference spectral information can be recorded at an interval of time with respect to one another which is not greater than a predetermined period, as noted above. Comparable or identical recording conditions apply to both sections or both items of spectral information both as a result of the local proximity and as a result of the temporal proximity, with the result that the difference represents only the spectral difference and does not additionally represent difference components which result from different recording conditions (for instance lighting, degree of development of the crops or weeds, reflections of the ground etc.).

Both items of spectral information are acquired for the same ground state (wet or dry). If only one sensor is shaded (that is to say an observation section sensor, whereas the reference sensor is not shaded or vice versa) for instance, the measured spectral information can be suppressed or can be removed for further processing in order to avoid errors. The shading can be determined, for instance, by comparing acquired spectral information with an item of predefined spectral information. In this case, the difference between the spectral distribution of sunlight in the case of direct solar irradiation and the spectral distribution of sunlight in the case of indirect/shaded/scattered solar irradiation is used. The difference results, for instance, from the wavelength-dependent attenuation (that is to say dispersion), for instance caused by clouds.

The reference sensor may be fastened on a field area (for instance by means of a stand set up on the field area or a holder inserted into the ground). The reference sensor is aimed at this field area. The observation section or the at least one optical observation section sensor can be guided over this field area. Because both sensors are guided over the same field area, identical or comparable optical acquisition conditions result. In this case, the reference sensor is stationary, whereas the observation section sensor is movable, for example by virtue of the latter being fastened to a (self-propelled) agricultural utility vehicle or a (pulled) mobile agricultural apparatus. The term "stationary" does not exclude the fact that the fastening location can be changed.

There is no more than a predetermined period between a time at which the actual sensor information is acquired and a time at which the reference sensor information is acquired. As a result of the fact that the acquisition of the spectra is temporally correlated, it can be assumed that said spectra have been acquired under the same (or under sufficiently similar) acquisition conditions. Changes in the acquisition conditions which occur between the first and second times can be detected. These changes (for instance cloudless weather which changes to cloudy weather) can be mapped by means of predefined mapping of the change to a correction term which is combined with the difference or is concomitantly taken into account when mapping the difference. However, the relevant information may be rejected instead of corrected. This can relate to the reference spectral information in which case a previously acquired and buffered item of spectral information is used as the (currently) acquired spectral information instead of a new measurement.

The actual spectral information and the reference spectral information characterize at least one spectrum interval or different light wavelengths. In some embodiments, the spectral information represents a spectrum interval which comprises a visible region and/or an infrared region and/or an ultraviolet region. For example, the spectral information characterizes an interval in which the color yellow lies (for instance 580-600 nm), an interval in which the color green lies (for instance 525-575 nm), an interval in which the color red lies (for instance 650-790 nm) and/or an infrared region of approximately 800-1000 nm (or else 900-1200 nm or else 1000-1500 nm) and/or an ultraviolet region, for instance a region inside UV-A, UV-B and/or UV-C. The spectral information represents the intensity of the light for a plurality of wavelengths or wavelength intervals.

The actual spectral information and the reference spectral information may be represented as a value or as a sequence or tuple of values relating to different wavelengths. Since the spectral information can be represented by numerical statements, data processing can be easily implemented, for instance by means of a microprocessor.

The actual spectral information and the reference spectral information may be acquired using at least one color sensor and/or using at least one electronic camera. A color detection unit may be connected downstream of the camera. Said color detection unit determines the color values over the entire image or over an image section from the camera. In this case, the color detection unit can be designed to statically detect the frequency of different color intervals. In some embodiments, the color detection unit may have a histogram function which is used to detect the frequency of pixels having different color values.

Whereas the color sensor does not map the spectral information but rather determines the spectral information over the entire field of view of the sensor, a (color) image is first of all created by the camera. The color values of the pixels of the camera (or of an image region of the camera) are combined in the color detection unit to form the spectrum which is represented by the spectral information. As a result of the color detection unit, the (image-related) camera therefore becomes the color sensor which does not provide any image resolution. The color detection unit therefore averages the pixels of the camera in order to arrive at an overall spectrum which is output as spectral information.

In order to acquire the actual spectral information in particular, it is possible to use a plurality of sensors or cameras, the fields of view of which are arranged beside one another. The plurality of sensors are arranged, for instance, along a spray bar of a field sprayer, in particular in an equidistant manner, for example at a distance of 20-100 cm, preferably at a distance of 40-60 cm. As a result, an agricultural apparatus which is equipped with this multiplicity of cameras or sensors can acquire the actual spectral information for a plurality of observation sections or for a large overall observation section. The sensor or the camera can record the entire field of view, in which case an image section, for which the spectral information is acquired, can be input, for instance by means of a touch-sensitive screen, whereas sensor or image information outside the image section is not taken into account. The touch-sensitive screen is used to select the field of view of the observation section sensors.

An inclination sensor may be arranged on the at least one observation section sensor or the inclination sensor may be arranged on an agricultural apparatus on which the at least one sensor is situated, the inclination sensor being set up to sense the inclination of the apparatus or the orientation of the observation section sensor. When controlling the agricultural apparatus (for instance a field sprayer), the orientation of the observation section sensor and/or of the field sprayer with respect to the field can be taken into account. Since the sensor or the field sprayer is also aimed at an increasing or decreasing field of view area with increasing inclination with respect to the field according to a tangent function, this change in the size of the field of view needs to be taken into account during evaluation or control in conjunction with the distance between the sensor and the center of the inclined movement (axis of rotation).

The weed percentage may form the basis for initiating a spray application process. In this case, an initiation limit which is predefined by the user and corresponds to a weed infestation which can still be tolerated and above which spray is intended to be sprayed is taken into account. This initiation limit can be predefined by the threshold value of the mapping device provided that the mapping is based on a comparison with one (or more) threshold value(s).

A spray boom angle and the speed of travel (as described in the next section) are also taken into account. The spray boom angle is the angle of the spray boom or another holder to which the observation section sensor is fastened. The spray boom angle corresponds to the inclination and, in particular, the distance of the sensor with respect to the field. The speed of travel determines a rate action which is used to compensate for the distance covered by the observation section between the acquisition of the spectral information and the time at which the applied agent hits the field. Therefore, the nozzle can be controlled in a manner delayed by a period, the distance substantially being compensated for by the period.

The speed at which the agricultural apparatus or the at least one sensor is guided over the field also needs to be taken into account. At a first inclination, which is greater than a second inclination, the field sprayer is controlled with a greater (averaged) flow rate than at the second inclination. The dependence may be substantially approximated to an arc tan function (or its square). At a first speed, which is greater than a second speed, the field sprayer is controlled with a greater (averaged) flow rate than at the second speed. The dependence may be substantially linear.

Shading (or generally recording conditions) of the observation section and/or of the reference section can also be determined, for instance using the sensor or the camera (for capturing the observation section) itself or using a further light sensor. In the case of different shading (between the observation section and the reference section), the actual or reference spectral information or else the difference between the actual and reference spectral information can be adapted by means of arithmetic combination with a predefined lighting correction variable. The lighting correction variable results from the detected shading (or from the change in the recording conditions), for instance by means of predefined mapping. This mapping may be based on empirical data and may represent an influence component which results from different recording conditions.

However, if different shading is detected (that is to say shading of only the reference sensor or of only the at least one observation section sensor), the output weed percentage may not be changed. In other words, no current comparisons of current spectral information are carried out in the case of partial shading. Instead, weed percentages (or control signals corresponding to the latter) which were used before the detection of the shading are used. If both sensors are shaded or if the shading is removed, the method is carried out as mentioned at the outset.

The recording conditions (that is to say shading) may be input via an input interface in one specific embodiment, in addition to being sensed by means of a sensor, in order to give the user the opportunity to input information relating to different recording conditions (of the reference spectral information in comparison with the actual spectral information). These recording conditions which have been input are taken into account when evaluating the spectral information acquired by means of the sensor.

The input interface for the recording conditions may display, for instance, selectable symbols or terms representing different recording conditions for the observation section and for the reference section. As a result, the relevant recording condition can be input for each item of spectral information, with the result that said changes immediately result from the input of different recording conditions. The selectable or detectable recording conditions may be, for instance: no cloud cover/slightly overcast/very overcast/daylight/twilight precipitation/fog/ground wet/ground dry/shaded/direct solar irradiation. Since these recording conditions have effects on the spectrum of the irradiated light, this procedure can at least partially compensate for a resulting error. This concerns, in particular, the input of whether only the reference sensor or only the at least one input sensor is shaded or is aimed at a sunlit section (in particular cloudless).

Furthermore, the static reference sensor can be aligned with a reference section which does not have a weed percentage or has a weed percentage which does not require any treatment, for instance by virtue of the reference sensor being mounted in a manually movable manner or being arranged by means of a displaceable holder (stand or the like).

The color sensor for acquiring the reference spectral information (that is to say the reference sensor) can be coupled to a camera, with the result that an image of the field of view of the color sensor is captured by the camera. The reference section is thereby displayed to the user as an image (for instance on the touch-sensitive screen) and it is detected if the user wishes to record the reference spectral information for the current reference section. The reference sensor and the camera coupled (mechanically and functionally) to it are aimed at the same field of view. The visual display of the information output by the reference sensor in the form of a camera can be used by the operator to assure himself of the weed percentage of the reference section and to possibly select another reference section (by transferring or reorienting the reference sensor). The reference section can generally be configured such that it has an upper limit of the weed percentage, for instance by placing a quantity of weeds which can still be tolerated onto a section which is otherwise free of weeds. The upper limit marks the weed percentage which still does not require any treatment. Instead of placing weeds, it is possible to place a color chart onto the reference section, the color chart representing the percentage of weeds which can still be tolerated.

An agricultural control device which is designed, in particular, to carry out the method is described below. The agricultural control device may include a control device for agricultural or landscape maintenance, in particular for a field sprayer or a fertilizer spreader. For the use of a fertilizer spreader, the reference sensor should be in a region of the field which is, for example, in a good or poor nutritional state, for instance in a nutritional state which represents a lower limit above which the fertilizer needs to be spread.

The observation sensor or the downstream evaluation, as described below, can be configured to distinguish, on the basis of a comparison with predefined spectral data, whether the measured deviations from the reference values can be attributed to the nutritional state or weed infestation. As a result, it is possible to avoid plant protection agent from being delivered to crops to be fertilized or the situation is avoided in which crops with a low nutritional state are assessed as weeds. It is also possible to thereby avoid fertilizer being spread onto weeds, in which case the situation is avoided, in particular, in which a high weed percentage is incorrectly assessed as crops with a low nutritional state. The control device may include a control output via which the control device is able to control the amount or throughput of the connectable field sprayer or fertilizer spreader.

The agricultural control device has at least one optical observation section sensor, for instance at least one observation sensor section as described herein. A multiplicity of observation section sensors may be arranged along a row or along a plurality of parallel rows. In particular, one observation section sensor is provided for each nozzle of the agricultural apparatus (field sprayer or fertilizer spreader). The respective area into which each nozzle delivers fertilizer or plant protection agent corresponds to a field of view (that is to say observation section) of an observation section sensor which is assigned to this nozzle.

The agricultural control device may has an optical reference sensor, for instance a reference sensor as described here. The reference sensor is stationary and can be connected to the evaluation components (comparator, mapping) described below via a wireless transmission interface. The agricultural control device therefore has a reference sensor receiving interface which can be connected to the reference sensor as described. In some embodiments, the sensors are optical sensors and are set up to acquire spectral information from the field of view of the relevant sensor.

The reference sensor receiving interface is fastened to the same vehicle as the observation section sensor. The reference sensor itself is stationary and can be connected or is connected to the reference sensor receiving interface via a wireless connection, for instance a radio connection.

In some embodiments, the agricultural control device includes a comparator connected downstream of the sensors. The comparator is set up to compare actual spectral information from the observation section sensor with reference spectral information from the optical reference sensor. The comparator is possibly set up to compare actual spectral information from the at least one observation section sensor with reference spectral information received via the reference sensor receiving interface.

In some embodiments, there are a plurality of observation section sensors, each connected to a comparator subunit of the comparator. The reference spectral information or a signal derived therefrom is transmitted to each comparator subunit via a data bus. The data bus connects the reference sensor receiving interface to the comparator subunits. In this manner, the data bus distributes the reference spectral information among the comparator subunits of the comparator. Each comparator subunit is in the form of a separate (physically individual) module which is arranged, in particular, on the associated nozzle.

Such a module may also possibly have, in addition to the associated sensor, an associated mapping subunit. A nozzle may be assigned to each module. Each comparator subunit is connected to an observation section sensor, the observation section of which (that is to say the field of view of which) is aimed at a section into which the nozzle is also aimed. The nozzle comprises an electrically controllable valve. The latter is (indirectly) controlled by the associated comparator subunit of the comparator. Control is effected via a mapping unit or a plurality of mapping subunits of the mapping unit, as described below. In some embodiments, the agricultural control device includes a mapping unit which is connected downstream of the comparator.

The mapping unit is set up to map the comparison result from the comparator to a weed percentage and to output it at an output of the agricultural control device. This output is the control output, in particular. The mapping unit may have a map, for instance in the form of a look-up table or an approximation formula, but may be in the form of a threshold value comparator. The mapping assigns different comparison results to individual weed percentages. The basis for the mapping may be an empirical acquisition of the ratio of weed percentages to differences between actual and reference spectra.

The weed percentage can be represented as an area percentage in the sense of weed growth/crop growth, can be represented as a mass percentage of weed growth/crop growth, or can be represented as a more in-depth variable, for instance in the sense of the amount of plant protection agent to be applied, which directly results from the area-based or mass-based weed percentage. In particular, the weed percentage can be directly in the form of a control variable for the relevant nozzle and can therefore directly correspond to a control variable.

The mapping unit has a plurality of mapping subunits, in particular. One mapping subunit is provided for each nozzle or for each observation section sensor (e.g., each observation section).

An individual mapping subunit may be connected downstream of each comparator subunit. A control connection of an associated nozzle is assigned to each mapping subunit. Each mapping subunit may be in the form of a (physically independent) module. A mapping subunit and a comparator subunit (connected upstream of the latter) may be connected upstream of each nozzle.

Each mapping subunit and the associated comparator subunit may be in the form of a (physically independent) evaluation module. An associated nozzle is connected downstream of each evaluation module, for instance via a control output of the evaluation module. Each evaluation module comprises (at least) two data inputs or a combined data input set up to receive actual and reference spectral information, in particular a bus connection for connection to the reference receiving interface and a connection for the associated observation section sensor (which, like the associated nozzle as well, is aimed at the relevant observation section).

A further activation input may be provided for each nozzle or for each evaluation module, which activation input is connected to a user input interface or a corresponding input channel which can be used by the operator to input an activation command or deactivation command for a nozzle or a group of nozzles. This command is executed by the nozzle or the evaluation module independently of the relevant weed percentage; the activation input therefore has priority over the evaluation module. The activation input may also be in the form of a control input, as described below.

The mapping unit or the agricultural control device may have a further control input which can be used to input operator or control specifications (for instance a basic amount or a basic throughput). The agricultural control device and, in particular, the mapping unit are set up to combine the mapping result (that is to say the weed percentage determined by the mapping unit) with the operating specifications in order to output a control signal which has been combined in this manner at the output. For this purpose, the agricultural control device or the mapping unit may have a combining device which is preferably on the output side, for instance an adder which can have weighted inputs, for example. The control input indicates, for instance, a basic amount or a duty ratio for defining the open and closed state of the relevant nozzle or the relevant group of nozzles.

As mentioned, the agricultural control device may have a reference sensor receiving interface. The latter is set up to be connected to an optical reference sensor (which is external or belongs to the agricultural control device) via a wireless data connection. The reference sensor mentioned above may be designed like a reference sensor described here.

The optical reference sensor may comprise a static sensor. As mentioned, the static reference sensor may be a component which is outside the agricultural control device, or, in another embodiment, may be considered to be a (physically unconnected) part of the agricultural control device.

A color detection unit (or a subunit of the latter) may be connected downstream of the reference sensor receiving interface or the optical reference sensor or else the observation section sensor. A color detection subunit may be connected upstream of each comparator subunit. These subunits may be integrated together in said evaluation module.

In some embodiments, there is a verification unit connected to a plurality of comparator or mapping subunits. It compares, in particular, the actual spectral information from the individual observation section sensors and detects when said information has differences which are greater than a predetermined threshold value. It is therefore possible to detect partial shading, that is to say shading of individual observation sections or of a plurality of observation sections which does not apply to all observation sections. The verification unit is set up, by means of the threshold value (or by means of a corresponding threshold value vector for a plurality of spectral sections), to detect spectral changes typical of shading and therefore to determine whether one observation section is shaded, while another is not shaded. The verification unit is also connected to the mapping subunits and to the nozzles in a controlling manner to disconnect at least the relevant nozzles or to still also keep the previously used activation state of the nozzle if partial shading is detected until the verification unit no longer determines any partial shading.

If partial shading is not detected, the verification unit does not intervene in the control of the nozzles or in the evaluation by the comparator or the mapping. The verification unit may also be set up to form an average value (or an average value vector) of all actual spectral information in the sense of an ensemble average value for the observation sensors. This may be predefined to the individual comparator subunits as actual spectral information, in particular if shading is detected. Instead of an average value, it is also possible to use a median.

FIG. 1 illustrates an application environment and is used to explain an embodiment of the method for determining a weed percentage. Crops N and weeds U are situated in an observation section 10 which is guided over an agricultural field 20, the weed percentage varying with movement over the field 20. The field 20 is part of a ground area 22. More plant protection agent is intended to be applied in regions in which there are weeds U, for instance in the region 24, than in regions in which there are fewer weeds or no weeds.

For this purpose, the observation section 10 is guided over the field 20 by guiding at least one observation section sensor, here two observation section sensors 12a, b by way of example, over the field, for example by means of a tractor or a trailer. The observation section 10 results from the fields of view of the observation section sensors 12a, b which are aimed at the field 20. The observation section sensors 12a, b may comprise optical sensors and determine actual spectral information for light which is reflected into the sensors 12a, b by the field. Therefore, sunlight or other ambient light is used to evaluate the actual spectral information. In particular, no light sources which are used exclusively to evaluate the spectral information are provided. The spectral information relates to visible light and may also comprise UV or IR spectral components.

Since the light which is used for evaluation changes on the basis of the weather conditions and the spectrum of the light on the ground area 22 is therefore also variable, reference spectral information is acquired by means of an optical reference sensor 32 which is aimed at a reference section 30 of the same ground area 22. The difference between the actual spectral information and the reference spectral information is determined and the weed percentage is inferred from the difference.

In this case, mapping which assigns different weed percentages to a plurality of differences is used, in particular. Instead of an assignment to weed percentages, it is possible to map directly to a control variable (flow volume, mass, flow rate) of a field sprayer, a fertilizer spreader or another agricultural working device. This control variable is combined, in particular, with operator or control specifications (for instance a spraying duration, a basic amount or a basic throughput), or these operator or control specifications are changed according to the control variable mentioned at the outset, which results from the difference, and output in this changed form at an output, cf. FIG. 2. This output is designed to be connected to the agricultural working device in a controlling manner and is set up to output corresponding control signals to the working device. The output preferably outputs a plurality of signals, in particular a control signal for each nozzle of the working device, cf. FIG. 2. A change in the incidence of light on the field 20 (and therefore in the spectrum of the light) results in a change which similarly concerns the reference spectral information and the actual spectral information. Since this information similarly changes with the change in the incidence of light, this change is removed when forming the difference. The reference spectral information and the actual spectral information relate to the same ground area 22 and, in particular, the same field 20 and are therefore exposed to the same incidence of light.

The reference section 30 is part of the field 20 over which the observation section 10 is guided. Alternatively, it can be outside the field 20, but can be provided on the same ground area 22 as the field 20. The reference sensor 32 may be aimed at the field 20 and static (that is to say stationary). The reference sensor 32 may be held in a stationary manner, for instance using a stand or a holder 34 penetrating the field.

The reference sensor 32 may wirelessly transmit the reference spectral information. The reference sensor 32 has a wireless data transmission interface which is used to transmit the reference spectral information, in particular to a reference sensor receiving interface (cf. reference symbol 133 in FIG. 2) in order to make it possible to compare the reference spectral information with actual spectral information on board the tractor or the working device (in particular in the agricultural control device illustrated with reference symbol 100 in FIG. 2).

Figure 2:
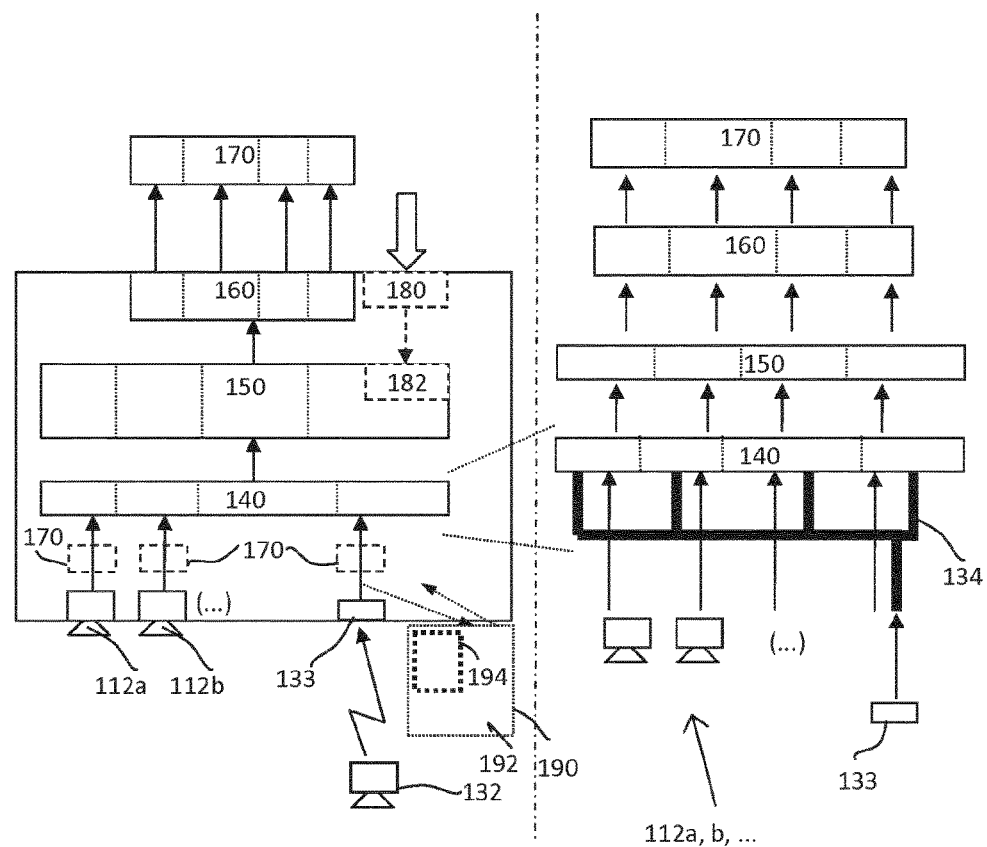
FIG. 2 shows an embodiment of the agricultural control device described here with some optional features.

FIG. 2 shows, to the left of the vertical dot-dashed line, an overview of an agricultural control device 100 and shows, to the right of the vertical dot-dashed line, details of the data flow when some of the components described below are subdivided into individual subunits. The agricultural control device 100 includes at least one optical observation section sensor, for instance the two observation section sensors 112a, b illustrated here.

The use of a plurality of observation section sensors 112a, b allows a wider region to be covered. The field of view of each sensor, e.g., each individual observation section, is aimed at a section into which an associated nozzle of the agricultural apparatus 170, for instance a field sprayer, is aimed. The plurality of sensors 112a, b may be evaluated individually or with individual modules (comprising a comparator subunit and a mapping subunit). The actual spectral information from the observation section sensors 112a, b is used individually and is respectively compared with the reference spectral information from the reference sensor 132.

In addition to the observation section sensors 112a, b, at least one optical reference sensor 132 or a reference sensor receiving interface 133 is part of the agricultural control device 100. The interface 133 is fastened to the same vehicle (or to the same tractor or the same working device) as the observation section sensors 112a, b. The optical reference sensor 132 is stationary, in a manner corresponding to the reference sensor 32 in FIG. 1. The reference sensor receiving interface 133 is mobile and is set up to wirelessly receive data, which represent the reference spectral information, from the stationary reference sensor 132. The stationary reference sensor 132 can be considered to be part of the agricultural control device 100, as illustrated in FIG. 2.

In some embodiments, only the reference sensor receiving interface, and not the stationary reference sensor, is a physical part of the agricultural control device, the reference sensor receiving interface undertaking the task of acquiring the reference spectral information for the purpose of carrying out the comparison. The vehicle and the tractor and the working device may not be part of the agricultural control device 100, but rather are used to explain the physical relationship of the sensors with respect to one another and the relationship of the sensors/the interface with respect to the field.

The comparator 140 may be connected downstream of the sensors 112a, b and 132 and the interface 133. The comparator 140 is set up to compare actual spectral information from the at least one observation section sensor 112a, b with reference spectral information from the optical reference sensor 132, 132'. The comparator 140 is divided into individual subunits, as is illustrated using the dotted lines. Each subunit is fastened to the relevant nozzle of the agricultural apparatus 170 or to a holder which carries the nozzle. The agricultural apparatus 170 is subdivided into subsections which correspond to individual nozzles or groups of nozzles. The comparator 140 may compare actual spectral information with data received at the interface 133.

In some embodiments, a mapping unit 150 of the agricultural control device is connected downstream of the comparator 140. The mapping unit 150 provides as output the comparison result (or the comparison results if the actual spectral information is processed in a sensor-specific manner) from the comparator at an output 160 of the control device 100. The output 160 is set up such that a control input of a downstream working device (for example a field sprayer) can be connected.

In some embodiments, the mapping unit 150 is divided into individual subunits, as illustrated using the dotted lines. Each subunit is fastened to the relevant nozzle of the agricultural apparatus 170 or to a holder which carries the nozzle. The subunit of the mapping unit 140 and the subunit of the comparator 150 may comprise a module fitted to the associated nozzle or to its holder. The output 160 outputs a plurality of signals, e.g., a control signal for each nozzle of the working device, as illustrated using the subdivision on the basis of the dashed lines.

The agricultural control device 100 may have a further control input 180 to put in operator or control specifications (for instance a basic amount, a basic intensity, or a basic throughput). A combining device 182 receives the operator or control specifications (illustrated by the double arrow in the upper half of the image) and may arithmetically or logically combine the mapping result with the data received at the control input 180. This results in a combined control signal at the output 160, which control signal is composed of the operator or control specifications and the mapping result (that is to say the weed percentage). This combination can be considered, in particular, to be a modification of the operator or control specifications. Since the weed percentage is directly linked to a change in the amount or the throughput, for instance of a field sprayer, these variables can be combined in the sense of a modification or correction of the operator or control specifications.

In particular, the combining device 182 may comprise a multiplier, with the result that the control specification is used to set the spraying amount, with which spraying is carried out or fertilizer is spread in the case of a high weed percentage (or low degree of development of the plant). If a low weed percentage or no weed percentage is determined, with the result that no delivery would be provided on the basis of the mapping result per se, a multiplication by a control specification would also result in no delivery of plant protection agent (or fertilizer) being controlled.

If the combining device 182 is in the form of an adder, a numerical representation of the weed percentage can be added to the operator or control specifications, which numerically represent a (basic) amount or a (basic) throughput of plant protection agent, with the result that the amount of plant protection agent to be applied is increased if the weed percentage is increased or vice versa. In other words, the operator or control specification is increased more in the case of a first weed percentage than in the case of the second weed percentage which is less than the first weed percentage. Furthermore, the operator or control specification is increased more in the case of a first difference between the spectra than in the case of the second difference which is less than the first difference. A high weed percentage corresponds to a long spraying duration or intensive delivery of plant protection agent (or fertilizer), whereas a smaller weed percentage than this corresponds to a shorter spraying duration or less intensive delivery.

In some embodiments, a color detection unit 170 is connected downstream of the at least one optical observation section sensor 112a, b and/or the reference sensor receiving interface 133 or the optical reference sensor 132' if the relevant sensor is in the form of a camera or an imaging system. The color detection unit 170 is situated between the sensor 112a, b; 132, 132' or the interface 133 and the comparator 140. In this case, the receiving interface 133, the reference sensor 132, 132' and/or the at least one optical observation section sensor 132 may be designed to record an electronic image or to receive image information. The color detection unit 170 may be designed as part of the camera which is converted in this manner as a color sensor.

The agricultural control device 100 may have a screen 190. The screen 190 may be connected downstream of the reference sensor 132 (or the interface 133), the reference sensor 132 being in the form of a camera in this case. This makes it possible for the reference section to be optically checked by the operator who can possibly select an image section 194 via an input apparatus 182 linked thereto, for instance to define the weed percentage which can be tolerated. For this purpose, the screen generally has an input apparatus which is illustrated in FIG. 2 as a touch-sensitive layer 192, but may also be implemented by means of an input device such as a keyboard, a computer mouse, a trackball, or a light pen. The reference spectral information relates, in particular, only to the section 194 if such a section is selected. The touch-sensitive layer 192 and the screen 190 below together form a touch-sensitive display.

In some embodiments, the sensor 132 comprises an electronic camera to record color spectra of the visible light into the infrared range. The color detection unit 170 statistically evaluates individual pixel color information relating to the relevant image in order to determine the spectrum or the spectrum information for the entire image or else only for an image section. In this case, a histogram of the color values, for instance, may be created for all relevant pixels by the color detection unit 170, the histogram (or parts of the latter) corresponding to the spectrum information. If appropriate, the sensors 112a, b may also be in the form of cameras provided that they have a sufficient recording rate. In some embodiments, there is an inclination sensor sensing the inclination of the sensors 112a, b and 132 and of the agricultural apparatus. If the agricultural apparatus (to which the sensors 112a, b are fastened) pivots upward, this movement and the resulting change in the orientation of the sensors are taken into account. The agricultural control device 100 may have a speed input to receive a speed signal representing the speed at which the observation field sensors 112a, b are guided over the field. A separate, in particular radar-based, speed sensor may be connected to the speed input, which speed sensor determines the speed of the observation section over ground. Alternatively, a CAN bus of the vehicle can be connected, in which bus numerous data items, in particular speed information, are transmitted between components of the vehicle. The vehicle's own speed sensor is therefore used in the last-mentioned case.

If the center of the field of view of the observation field sensors 112a, b and the orientation of the nozzles or of the agricultural apparatus diverge, a delay is introduced when converting the determined weed percentage (that is to say when controlling the nozzles), which delay depends on this speed. As a result, the distance covered between the detection of the observation section and the time at which the agricultural apparatus or the nozzle(s) is/are guided over this observation section is taken into account (or compensated for).

The image half to the right of the dot-dashed line in FIG. 2 shows, in detail, the observation sensors 112a, b (by way of example) which supply the respective actual spectral information to individual subunits of the comparator 140 (see dotted line subdivision) according to the illustrated arrows. The receiving interface 133 receives the reference spectral information and distributes it to the individual subunits of the comparator 140 via the bus 134 (illustrated by thicker lines). The subunits of the comparator 140 (which can also be referred to as comparator subunits) may be each connected upstream of subunits of the mapping unit 150, as is illustrated using the arrows.

In a simple case, the mapping unit 150 comprises an input for a threshold value or a threshold value vector to which the sensitivity of the mapping unit (that is to say the sensitivity to weeds) is set. An output 160 is connected downstream of the mapping unit 150 and is used to output individual control signals, as is illustrated by the subdivision (see dotted lines). The output 160 can be subdivided into individual subunits which are physically independent, in particular. Subunits of the comparator, of the mapping unit and of the output which are assigned to the same observation section sensor 112a can be provided as a (physically independent) module. Like the observation section sensor 112a as well, this is fastened to a holder on which the nozzle which is controlled by the relevant subsection of the output is situated. In this case, the subsections of the output 160, of the mapping unit 150 and of the comparator are autonomous for each observation section sensor 112a. The observation section sensor 112a and the associated subsections can be mounted in the same housing.

FIG. 2 is only a schematic functional illustration and is not suitable for defining physical properties and arrangements.

What is claimed is:

1. A method for determining a weed percentage in an observation section of a field, the method comprising:
    acquiring actual spectral information using an optical observation section sensor aimed at the observation section;
    acquiring reference spectral information using an optical reference sensor aimed at a reference section of the same ground area;
    determining a difference between the actual spectral information and the reference spectral information; and
    mapping the difference to the weed percentage using predefined mapping.

2. The method as claimed in claim 1, wherein the reference section and the observation section comprise regions of the same field and are arranged close together or at least partially overlapping.

3. The method as claimed in claim 1, further comprising the reference sensor fastened on an area of the field over which the observation section or the optical observation section sensor is guided.

4. The method as claimed in claim 1, wherein the actual spectral information and the reference spectral information characterize a spectrum interval, and the actual spectral information and the reference spectral information include a respective value or sequence of values relating to different wavelengths of light.

5. The method as claimed in claim 1, further comprising acquiring the actual spectral information or the reference spectral information using color sensors or electronic cameras; and
    determining color values over the entire image or over an image section from the cameras with a color detection unit connected downstream of the cameras.

6. The method as claimed in claim 1, further comprising determining shading of the observation section and of the reference section; and
    in the event of different shading, adapting either (a) the actual spectral information, or (b) the reference spectral information, or (c) the difference between the actual and reference spectral information by means of arithmetic combination with a predefined lighting correlation variable.

7. The method as claimed in claim 1, further comprising aligning the reference sensor with a reference area which does not have a weed percentage or has a tolerable weed percentage.

8. An agricultural control device (100) having
    an optical observation section sensor;
    a reference sensor receiving interface;
    an optional optical reference sensor;
    the observation section sensor and the reference sensor receiving interface fastened to a vehicle;
    a comparator connected downstream of the sensors to compare actual spectral information from the observation section sensor with reference spectral information from the optical reference sensor; and
    a mapping unit connected downstream of the comparator to map the comparison result from the comparator to a weed percentage and to provide the mapped result to an output of the agricultural control device.

9. The agricultural control device as claimed in claim 8, further comprising the reference sensor receiving interface connected to the optical reference sensor via a wireless data connection.

10. The agricultural control device as claimed in claim 8, further comprising:
    a color detection unit connected downstream of the optical observation section sensor or the reference sensor receiving interface; and
    the reference sensor or the optical observation section sensor recording an electronic image and the receiving interface receiving the electronic image.

* * * * *